(12) United States Patent
Jaehne et al.

(10) Patent No.: US 6,410,577 B2
(45) Date of Patent: Jun. 25, 2002

(54) SUBSTITUTED 8,8A-DIHYDRO-3AH-INDENO [1,2-D]THIAZOLES, PROCESSES FOR THEIR PREPARATION AND THEIR USE AS MEDICAMENTS

(75) Inventors: Gerhard Jaehne, Frankfurt; Hans-Jochen Lang; Matthias Gossel, both of Hofheim; Martin Bickel, Bad Homburg, all of (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 52 days.

(21) Appl. No.: 09/790,905

(22) Filed: Feb. 23, 2001

(30) Foreign Application Priority Data

Feb. 23, 2000 (DE) .......................................... 100 08 274

(51) Int. Cl.⁷ ..................... C07D 277/60; A61K 31/425
(52) U.S. Cl. ......................................... 514/366; 548/150
(58) Field of Search ............................ 548/150; 514/366

(56) References Cited

U.S. PATENT DOCUMENTS

| | | | |
|---|---|---|---|
| 3,507,868 A | | 4/1970 | Manning |
| 6,235,763 B1 | * | 5/2001 | Jaehne ........................ 514/366 |

FOREIGN PATENT DOCUMENTS

| | | |
|---|---|---|
| EP | 0 749 966 A1 | 12/1996 |
| FR | 2 338 937 A1 | 8/1977 |
| FR | 2 364 219 A1 | 4/1978 |
| WO | WO 00/18749 A1 | 4/2000 |
| WO | WO 00/51994 A1 | 9/2000 |

* cited by examiner

Primary Examiner—Robert Gerstl
(74) Attorney, Agent, or Firm—Heller Ehrman White and McAuliffe

(57) ABSTRACT

The invention relates to substituted 8,8a-dihydro-3aH-indeno[1,2-d]thiazoles and to their physiologically acceptable salts and physiologically functional derivatives. Compounds of formula I,

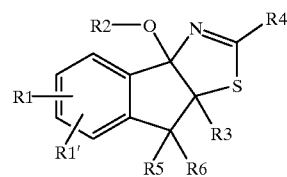

in which the radicals are as defined above, and their physiologically acceptable salts and processes for their preparation are described. The compounds are suitable, for example, as anorectics.

32 Claims, No Drawings

SUBSTITUTED 8,8A-DIHYDRO-3AH-INDENO[1,2-D]THIAZOLES, PROCESSES FOR THEIR PREPARATION AND THEIR USE AS MEDICAMENTS

This application claims priority to German Application No. 10008274.2 filed Feb. 23, 2000, the entire contents of which are hereby incorporated by reference.

FIELD OF THE INVENTION

The invention relates to substituted 8,8a-dihydro-3aH-indeno[1,2-d]thiazoles and to their physiologically acceptable salts and physiologically functional derivatives.

BACKGROUND OF THE INVENTION

Thiazolidine derivatives having anorectic action have already been described in the prior art (Austrian patent No. 365181).

The object of the invention is to provide compounds having a therapeutically useful anorectic action. The present compounds also find use in treatment of type II diabetes and obesity.

SUMMARY OF THE INVENTION

The invention relates to compounds of formula I:

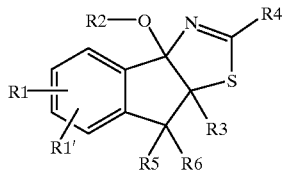

(I)

in which

R1, R1' are independently selected from H, F, Cl, Br, I, $CF_3$, $NO_2$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, O—$(C_1-C_6)$-alkyl, wherein one or more of the hydrogens of the alkyl, alkenyl, or alkynyl radicals may be replaced by fluorine, or one hydrogen may be replaced by OH, $OC(O)CH_3$, $OC(O)H$, O—$CH_2$—Ph, $NH_2$, NH—CO—$CH_3$ or $N(COOCH_2Ph)_2$;

$SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl, $SO_2$—$(CH_2)_n$-phenyl, wherein n is 0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$;

$NH_2$, NH—$(C_1-C_6)$-alkyl, $N[(C_1-C_6)$-alkyl$]_2$, $NH(C_1-C_7)$-acyl, phenyl, biphenylyl, O—$(CH_2)_n$-phenyl, where n is 0–6, 1- or 2-naphthyl, 2-, 3- or 4-pyridyl, 2- or 3-furanyl or 2- or 3-thienyl, wherein any of the phenyl, biphenyl, naphthyl, pyridyl, furanyl or thienyl rings may be optionally substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N[(C_1-C_6)$-alkyl$]_2$, $SO_2$—$CH_3$, COOH, COO—$(C_1-C_6)$-alkyl or $CONH_2$;

1,2,3-triazol-5-yl, wherein the triazole ring may be substituted in the 1-, 2- or 3-position by methyl or benzyl; tetrazol-5-yl, where the tetrazole ring may be substituted in the 1- or 2-position by methyl or benzyl; 1,3,4-oxadiazol-2-yl; 2-amino-1,3,4-oxadiazol-5-yl, wherein the amino function may be mono- or disubstituted by $(C_1-C_6)$-alkyl, —C(O)—$(C_1-C_6)$-alkyl, —C(O)—(cyclo-$C_3$-$C_7$)-alkyl, —C(O)-phenyl, —C(O)—NH—$(C_1-C_6)$-alkyl, —C(O)—NH—(cyclo-$C_3$-$C_7$)-alkyl, or —C(O)—NH-aryl, wherein aryl is phenyl, 2-, 3- or 4-pyridyl, 2- or 3-thienyl or 2- or 3-furanyl, —C(O)-morpholin-4-yl, —C(O)-piperidin-1-yl, —C(O)-piperazin-4-yl, —C(O)—1-methyl-, 1-benzyl-piperazin-4-yl, —$SO_2$—$(C_1-C_6)$-alkyl or —$SO_2$-phenyl, wherein the phenyl ring may be substituted up to two times by F, Cl, Br, CN, $CF_3$, OH, $OCF_3$, $(C_1-C_6)$-alkyl, O—$(C_1-C_6)$-alkyl, $(CH_2)_n$-phenyl, O—$(CH_2)_n$-phenyl, where n is 0–6, $NH_2$, $NH(C_1-C_6)$-alkyl, $N[(C_1-C_6)$-alkyl$]_2$, $SO_2$—$CH_3$, COOH, COO—$(C_1-C_6)$-alkyl or $CONH_2$;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(C_1-C_6)$-alkyl, C(O)—$(C_3-C_6)$-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl, wherein n is 0–5 and in which any of phenyl, thienyl, pyridyl or furyl may be optionally substituted up to two times by Cl, F, CN, $CF_3$, $(C_1-C_3)$-alkyl, OH or O—$(C_1-C_6)$-alkyl;

R3 is H, $(C_1-C_6)$-alkyl, F, Cl, Br, CN, $N_3$, O—$(C_1-C_6)$-alkyl, $(CH_2)_n$-phenyl, $(CH_2)_n$-thienyl, $(CH_2)_n$-pyridyl, $(CH_2)_n$-furyl, where n is 0–5 and in which any of phenyl, thienyl, pyridyl or furyl may be optionally substituted up to two times by Cl, F, CN, $CF_3$, $(C_1-C_3)$-alkyl, OH or O—$(C_1-C_6)$-alkyl, $(C_2-C_6)$-alkynyl, $(C_2-C_6)$-alkenyl, $OC(O)CH_3$, $(CH_2)_n$—$C(O)O(C_1-C_6)$-alkyl, $(CH_2)_n$—C(O)OH, $(CH_2)_n$—$C(O)NH_2$, $(CH_2)_n$—$C(O)NHCH_3$ or $(CH_2)_n$—$C(O)N(CH_3)_2$, where n is 0–3;

R4 is $(C_1-C_8)$-alkyl, $(C_3-C_7)$-cycloalkyl, $(C_2-C_6)$-alkenyl, $(C_2-C_6)$-alkynyl, $(C_4-C_7)$-cycloalkenyl, wherein one or more of the hydrogens of the alkyl radicals may be replaced by fluorine or one hydrogen may be replaced by OH, $OC(O)CH_3$, $OC(O)H$, O—$CH_2$—Ph or O—$(C_1-C_4)$-alkyl; is $(CH_2)_n$-pyrrolidin-1-yl, $(CH_2)_n$-piperidin-1-yl, $(CH_2)_n$-morpholin-4-yl, $(CH_2)_n$-piperazin-1-yl, $(CH_2)_n$-N-4-methylpiperazin-1-yl, $(CH_2)_n$—N-4-benzylpiperazin-1-yl, $(CH_2)_n$-phthalimidoyl, where n is 1–6;

$(CH_2)_n$-aryl or $(CH_2)_n$-heteroaryl, where n is 0–6 and aryl is phenyl, biphenylyl or 1- or 2-naphthyl and heteroaryl is 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl, wherein the aryl radical or the heteroaryl radical may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $(CH_2)_n$—$SO_2$—$(C_1-C_6)$-alkyl, $(CH_2)_n$—$SO_2$—$NH_2$, $(CH_2)_n$—$SO_2$—N(=CH—$N(CH_3)_2$), wherein n is 0–6, $(C_1-C_6)$-alkyl, $(C_3-C_6)$-cycloalkyl, COOH, $COO(C_1-C_6)$-alkyl, COO $(C_3-C_6)$-cycloalkyl, $CONH_2$, $CONH(C_1-C_6)$-alkyl, CON[($C_1$–$C_6$)-alkyl]$_2$, CONH($C_3$–$C_6$)-cycloalkyl, NH$_2$, NH—CO—($C_1$–$C_6$)-alkyl, NH—CO-phenyl, NH—SO$_2$—($C_1$–$C_6$)-alkyl, NH—SO$_2$-phenyl, wherein the phenyl ring may be substituted up to two times by F, Cl, CN, OH, ($C_1$–$C_6$)-alkyl, O—($C_1$–$C_6$)-alkyl, CF$_3$, COOH, COO($C_1$–$C_6$)-alkyl or CONH$_2$;

pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl or SO$_2$—(CH$_2$)$_n$-phenyl, wherein n is 0–3;

(CH$_2$)$_n$—A—R8, wherein n is 1–6;

A is O, NH, N—($C_1$–$C_6$)-alkyl, NCHO, N(CO—CH$_3$), S, SO or SO$_2$;

R8 is ($C_1$–$C_8$)-alkyl, ($C_3$–$C_8$)-cycloalkyl, wherein one or more hydrogens of the alkyl radicals may be replaced by fluorine or one hydrogen may be replaced by OH, OC(O)CH$_3$, OC(O)H, O—CH$_2$—Ph or O—($C_1$–$C_4$)-alkyl; is (CH$_2$)$_m$-aryl, wherein m is 0–6 and aryl is phenyl, thienyl or pyridyl and the aryl moiety may be optionally substituted up to two times by F, Cl, Br, OH, CF$_3$, NO$_2$, CN, OCF$_3$, O—($C_1$–$C_6$)-alkyl, S—($C_1$–$C_6$)-alkyl, SO—($C_1$–$C_6$)-alkyl, (CH$_2$)$_n$—SO$_2$—($C_1$–$C_6$)-alkyl, (CH$_2$)$_n$—SO$_2$—NH$_2$, (CH$_2$)$_n$—SO$_2$—N(=CH—N(CH$_3$)$_2$), (CH$_2$)$_n$—SO$_2$—NH($C_1$–$C_8$)-alkyl, (CH$_2$)$_n$—SO$_2$—N[($C_1$–$C_8$)-alkyl]$_2$, (CH$_2$)$_n$—SO$_2$—NH($C_3$–$C_8$)-cycloalkyl, (CH$_2$)$_n$—SO$_2$—N[($C_3$–$C_8$)-cycloalkyl$_2$], where n is 0–6, ($C_1$–$C_6$)-alkyl, ($C_3$–$C_6$)-cycloalkyl, COOH, COO($C_1$–$C_6$)-alkyl, COO($C_3$–$C_6$)-cycloalkyl, CONH$_2$, CONH($C_1$–$C_6$)-alkyl, CON[($C_1$–$C_6$)-alkyl]$_2$, CONH($C_3$–$C_6$)-cycloalkyl, NH$_2$, NH($C_1$–$C_6$)-alkyl, N[($C_1$–$C_6$)-alkyl]$_2$, NH—CO—($C_1$–$C_6$)-alkyl, NH—CO-phenyl, NH—SO$_2$-phenyl, where the phenyl ring may be optionally substituted up to two times by F, Cl, CN, OH, ($C_1$–$C_6$)-alkyl, O—($C_1$–$C_6$)-alkyl, CF$_3$, COOH, COO($C_1$–$C_6$)-alkyl or CONH$_2$;

NH—SO$_2$—($C_1$–$C_8$)-alkyl, N($C_1$–$C_6$)-alkyl-SO$_2$—($C_1$–$C_8$)-alkyl, pyrrolidin-1-yl, morpholin-1-yl, piperidin-1-yl, piperazin-1-yl, 4-methylpiperazin-1-yl, (CH$_2$)$_p$-phenyl, O—(CH$_2$)$_p$-phenyl, S—(CH$_2$)$_p$-phenyl or SO$_2$—(CH$_2$)$_p$-phenyl, wherein p is 0–3;

R5 is H;

R6 is Cl, Br, OH, O—($C_1$–$C_6$)-alkyl, O—(CH$_2$)$_n$-aryl, O—(CH$_2$)$_n$-heteroaryl wherein n is 0–6 and aryl is phenyl and heteroaryl is 2-, 3- or 4-pyridyl or 2- or 3-thienyl;

O—C(O)—H, O—C(O)—($C_1$–$C_6$)-alkyl, O—C(O)—($C_3$–$C_8$)-cycloalkyl, O—C(O)-aryl, O—C(O)-heteroaryl, wherein aryl is phenyl and heteroaryl is pyridyl, thienyl or furanyl; O-alpha- or -beta-glucuronic acid, SH, S—($C_1$–$C_6$)-alkyl, S—(CH$_2$)$_n$-phenyl, wherein n is 0–6, S—C(O)—($C_1$–$C_6$)-alkyl, S—C(O)—($C_3$–$C_8$)-cycloalkyl, S—C(O)-phenyl; SO—($C_1$–$C_6$)-alkyl, SO—(CH$_2$)$_n$-phenyl, wherein n is 0–6, SO$_2$—($C_1$–$C_6$)-alkyl, SO$_2$—(CH$_2$)$_n$-phenyl, wherein n is 0–6, NH$_2$, NH—($C_1$–$C_6$)-alkyl, NH—($C_3$–$C_7$)-cycloalkyl, N[($C_1$–$C_6$)-alkyl]$_2$, morpholin-4-yl, pyrrolidin-1-yl, piperidin-1-yl, piperazin-1-yl, 1-methylpiperazin-4-yl, 1-benzylpiperazin-4-yl, NH-phenyl, NH—CH$_2$-phenyl, NH—C(O)—($C_1$–$C_6$)-alkyl or NH—C(O)-phenyl;

or

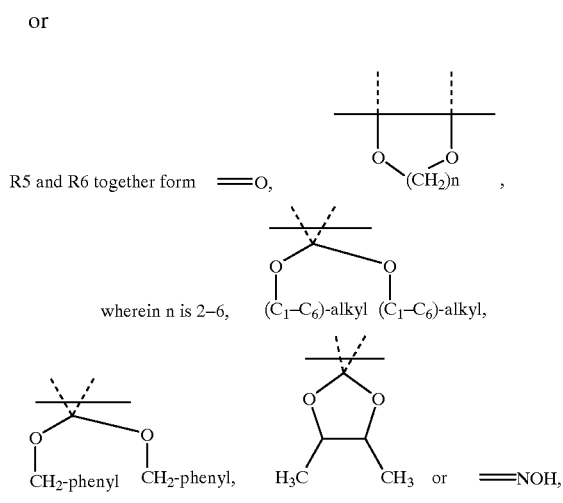

R5 and R6 together form =O, (CH$_2$)n, wherein n is 2–6, ($C_1$–$C_6$)-alkyl ($C_1$–$C_6$)-alkyl, CH$_2$-phenyl CH$_2$-phenyl, H$_3$C CH$_3$ or =NOH, and their physiologically acceptable salts and physiologically functional derivatives.

The invention also relates to pharmaceutical compositions containing the compounds of formula I and pharmaceutically acceptable carriers. Also, pharmaceutical compositions containing the compounds of formula I in combination with at least one additional anorectic agents are contemplated. The invention envisages treatment of obesity via administration of compounds of formula I. Methods of treatment for type II diabetes are also contemplated.

DETAILED DESCRIPTION OF THE INVENTION

The invention is directed to polycyclic thiazole compounds which are anorectics and are useful in the treatment of type II diabetes and obesity. The compounds have general formula (I):

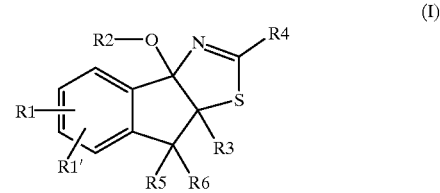

(I)

in which

R1, R1' are independently selected from H, F, Cl, Br, I, CF$_3$, NO$_2$, CN, COOH, COO($C_1$–$C_6$)-alkyl, CONH$_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl, O-($C_1$–$C_6$)-alkyl, wherein one or more of the hydrogens of the alkyl, alkenyl, or alkynyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH($C_1$–$C_6$)-alkyl, SO$_2$N[($C_1$–$C_6$)-alkyl]$_2$, S—($C_1$–$C_6$)-alkyl, S—(CH$_2$)$_n$-phenyl, SO—($C_1$–$C_6$)-alkyl, SO—(CH$_2$)$_n$-phenyl, SO$_2$—($C_1$–$C_6$)-alkyl, SO$_2$—(CH$_2$)$_n$-phenyl, wherein n is 0–6 and the phenyl radical may be substituted up to two times by F, Cl, Br, OH, CF$_3$, NO$_2$, CN, OCF$_3$, O—($C_1$–$C_6$)-alkyl, ($C_1$–$C_6$)-alkyl or NH$_2$;

NH$_2$, NH—($C_1$–$C_6$)-alkyl, N[($C_1$–$C_6$)-alkyl]$_2$, NH($C_1$–$C_7$)-acyl, phenyl, biphenylyl, O—(CH$_2$)$_n$-phenyl, where n is 0–6, 1- or 2-naphthyl, 2-, 3- or 4-pyridyl, 2- or 3-furanyl or 2- or 3-thienyl, wherein any of the phenyl, biphenyl, naphthyl, pyridyl, furanyl or thienyl rings may be optionally substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N[(C_1-C_6)$-alkyl$]_2$, $SO_2$—$CH_3$, COOH, COO—$(C_1-C_6)$-alkyl or $CONH_2$;

1,2,3-triazol-5-yl, wherein the triazole ring may be substituted in the 1-, 2- or 3-position by methyl or benzyl; tetrazol-5-yl, where the tetrazole ring may be substituted in the 1- or 2-position by methyl or benzyl; 1,3,4-oxadiazol-2-yl; 2-amino-1,3,4-oxadiazol-5-yl, wherein the amino function may be mono- or disubstituted by $(C_1-C_6)$-alkyl, —C(O)—$(C_1-C_6)$-alkyl, —C(O)—(cyclo-$C_3-C_7$)-alkyl, —C(O)-phenyl, —C(O)—NH—$(C_1-C_6)$-alkyl, —C(O)—NH—(cyclo-$C_3-C_7$)-alkyl, or —C(O)—NH-aryl, wherein aryl is phenyl, 2-, 3- or 4-pyridyl, 2- or 3-thienyl or 2- or 3-furanyl, —C(O)-morpholin-4-yl, —C(O)-piperidin-1-yl, —C(O)-piperazin-4-yl, —C(O)—1-methyl-, 1-benzyl-piperazin-4-yl, —$SO_2$—$(C_1-C_6)$-alkyl or —$SO_2$-phenyl, wherein the phenyl ring may be substituted up to two times by F, Cl, Br, CN, $CF_3$, OH, $OCF_3$, $(C_1-C_6)$-alkyl, O—$(C_1-C_6)$-alkyl, $(CH_2)_n$-phenyl, O—$(CH_2)_n$-phenyl, where n is 0–6, $NH_2$, $NH(C_1-C_6)$-alkyl, $N[(C_1-C_6)$-alkyl$]_2$, $SO_2$—$CH_3$, COOH, COO—$(C_1-C_6)$-alkyl or $CONH_2$;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(C_1-C_6)$-alkyl, C(O)—$(C_3-C_6)$-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl, wherein n is 0–5 and in which any of phenyl, thienyl, pyridyl or furyl may be optionally substituted up to two times by Cl, F, CN, $CF_3$, $(C_1-C_3)$-alkyl, OH or O—$(C_1-C_6)$-alkyl;

R3 is H, $(C_1-C_6)$-alkyl, F, Cl, Br, CN, $N_3$, O—$(C_1-C_6)$-alkyl, $(CH_2)_n$-phenyl, $(CH_2)_n$-thienyl, $(CH_2)_n$-pyridyl, $(CH_2)_n$-furyl, where n is 0–5 and in which any of phenyl, thienyl, pyridyl or furyl may be optionally substituted up to two times by Cl, F, CN, $CF_3$, $(C_1-C_3)$-alkyl, OH or O—$(C_1-C_6)$-alkyl, $(C_2-C_6)$-alkynyl, $(C_2-C_6)$-alkenyl, $OC(O)CH_3$, $(CH_2)_n$—$C(O)O(C_1-C_6)$-alkyl, $(CH_2)_n$—C(O)OH, $(CH_2)_n$—$C(O)NH_2$, $(CH_2)_n$—$C(O)NHCH_3$ or $(CH_2)_n$—$C(O)N(CH_3)_2$, where n is 0–3;

R4 is $(C_1-C_8)$-alkyl, $(C_3-C_7)$-cycloalkyl, $(C_2-C_6)$-alkenyl, $(C_2-C_6)$-alkynyl, $(C_4-C_7)$-cycloalkenyl, wherein one or more of the hydrogens of the alkyl radicals may be replaced by fluorine or one hydrogen may be replaced by OH, $OC(O)CH_3$, $OC(O)H$, O—$CH_2$—Ph or O—$(C_1-C_4)$-alkyl; is $(CH_2)_n$-pyrrolidin-1-yl, $(CH_2)_n$-piperidin-1-yl, $(CH_2)_n$-morpholin-4-yl, $(CH_2)_n$-piperazin-1-yl, $(CH_2)_n$-methylpiperazin-1-yl, $(CH_2)_n$—N-4-benzylpiperazin-1-yl, $(CH_2)_n$-phthalimidoyl, where n is 1–6;

$(CH_2)_n$-aryl or $(CH_2)_n$-heteroaryl, where n is 0–6 and aryl is phenyl, biphenylyl or 1- or 2-naphthyl and heteroaryl is 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl, wherein the aryl radical or the heteroaryl radical may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $(CH_2)_n$—$SO_2$—$(C_1-C_6)$-alkyl, $(CH_2)_n$—$SO_2$—$NH_2$, $(CH_2)_n$—$SO_2$—N(=CH—N($CH_3$)$_2$), wherein n is 0–6, $(C_1-C_6)$-alkyl, $(C_3-C_6)$-cycloalkyl, COOH, COO($C_1-C_6$)-alkyl, COO($C_3-C_6$)-cycloalkyl, $CONH_2$, $CONH(C_1-C_6)$-alkyl, CON$[(C_1-C_6)$-alkyl$]_2$, $CONH(C_3-C_6)$-cycloalkyl, $NH_2$, NH—CO—$(C_1-C_6)$-alkyl, NH—CO-phenyl, NH—$SO_2$-$(C_1-C_6)$-alkyl, NH—$SO_2$-phenyl, wherein the phenyl ring may be substituted up to two times by F, Cl, CN, OH, $(C_1-C_6)$-alkyl, O—$(C_1-C_6)$-alkyl, $CF_3$, COOH, COO($C_1-C_6$)-alkyl or $CONH_2$;

pyrrolidin-1-yl, morpholin-1-yl, piperidin-1-yl, piperazin-1-yl, 4-methylpiperazin-1-yl, $(CH_2)_n$-phenyl, O—$(CH_2)_n$-phenyl, S—$(CH_2)_n$-phenyl or $SO_2$—$(CH_2)_n$-phenyl, wherein n is 0–3;

$(CH_2)_n$-A-R8, wherein n is 1–6;

A is O, NH, N—$(C_1-C_6)$-alkyl, NCHO, N(CO—$CH_3$), S, SO or $SO_2$;

R8 is $(C_1-C_8)$-alkyl, $(C_3-C_8)$-cycloalkyl, wherein one or more hydrogens of the alkyl radicals may be replaced by fluorine or one hydrogen may be replaced by OH, $OC(O)CH_3$, $OC(O)H$, O—$CH_2$—Ph or O—$(C_1-C_4)$-alkyl; is $(CH_2)_m$-aryl, wherein m is 0–6 and aryl is phenyl, thienyl or pyridyl and the aryl moiety may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $(CH_2)_n$—$SO_2$—$(C_1-C_6)$-alkyl, $(CH_2)_n$—$SO_2$—$NH_2$, $(CH_2)_n$—$SO_2$—N(=CH—N($CH_3$)$_2$), $(CH_2)_n$—$SO_2$—$NH(C_1-C_8)$-alkyl, $(CH_2)_n$—$SO_2$—N$[(C_1-C_8)$-alkyl$]_2$, $(CH_2)_n$—$SO_2$—NH($C_3-C_8$)-cycloalkyl, $(CH_2)_n$—$SO_2$—N$[(C_3-C_8)$-cycloalkyl$_2]$, where n is 0–6, $(C_1-C_6)$-alkyl, $(C_3-C_6)$-cycloalkyl, COOH, COO($C_1-C_6$)-alkyl, COO($C_3-C_6$)-cycloalkyl, $CONH_2$, $CONH(C_1-C_6)$-alkyl, CON$[(C_1-C_6)$-alkyl$]_2$, $CONH(C_3-C_6)$-cycloalkyl, $NH_2$, $NH(C_1-C_6)$-alkyl, $N[(C_1-C_6)$-alkyl$]_2$, NH—CO—$(C_1-C_6)$-alkyl, NH—CO-phenyl, NH—$SO_2$-phenyl, where the phenyl ring may be optionally substituted up to two times by F, Cl, CN, OH, $(C_1-C_6)$-alkyl, O—$(C_1-C_6)$-alkyl, $CF_3$, COOH, COO($C_1-C_6$)-alkyl or $CONH_2$;

NH—$SO_2$—$(C_1-C_8)$-alkyl, $N(C_1-C_6)$-alkyl-$SO_2$—$(C_1-C_8)$-alkyl, pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, wherein p is 0–3;

R5 is H;

R6 is Cl, Br, OH, O—$(C_1-C_6)$-alkyl, O—$(CH_2)_n$-aryl, O—$(CH_2)_n$-heteroaryl wherein n is 0–6 and aryl is phenyl and heteroaryl is 2-, 3- or 4-pyridyl or 2- or 3-thienyl;

O—C(O)—H, O—C(O)—$(C_1-C_6)$-alkyl, O—C(O)—$(C_3-C_8)$-cycloalkyl, O—C(O)-aryl, O—C(O)-heteroaryl, wherein aryl is phenyl and heteroaryl is pyridyl, thienyl or furanyl; O-alpha- or -beta-glucuronic acid, SH, S—$(C_1-C_6)$-alkyl, S—$(CH_2)_n$-phenyl, wherein n is 0–6, S—C(O)—$(C_1-C_6)$-alkyl, S—C(O)—$(C_3-C_8)$-cycloalkyl, S—C(O)-phenyl; SO—$(C_1-C_6)$-alkyl, SO—$(CH_2)_n$-phenyl, wherein n is 0–6, $SO_2$—$(C_1-C_6)$-alkyl, $SO_2$—$(CH_2)_n$-phenyl, wherein n is 0–6, $NH_2$, NH—$(C_1-C_6)$-alkyl, NH—$(C_3-C_7)$-cycloalkyl, N[($C_1$–$C_6$)-alkyl]$_2$, morpholin-4-yl, pyrrolidin-1-yl, piperidin-1-yl, piperazin-1-yl, 1-methylpiperazin-4-yl, 1-benzylpiperazin-4-yl, NH-phenyl, NH—$CH_2$-phenyl, NH—C(O)—($C_1$–$C_6$)-alkyl or NH—C(O)-phenyl;
or

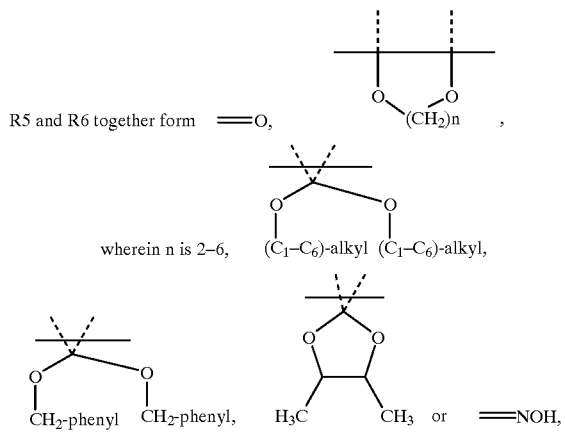

R5 and R6 together form =O, (CH$_2$)n wherein n is 2–6, ($C_1$–$C_6$)-alkyl ($C_1$–$C_6$)-alkyl, $CH_2$-phenyl $CH_2$-phenyl, $H_3C$ $CH_3$ or =NOH, and their physiologically acceptable salts and physiologically functional derivatives.

In a preferred embodiment, the compounds of formula I are where

R1, R1' are independently selected from H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl, O-($C_1$–$C_6$)-alkyl,
wherein one or more hydrogens of the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COOC$H_2$Ph)$_2$;
$SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl,
wherein n is 0–6 and the phenyl radical may be optionally substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$;
$NH_2$, NH—($C_1$–$C_6$)-alkyl, N[($C_1$–$C_6$)-alkyl]$_2$, NH($C_1$–$C_7$)-acyl, phenyl, biphenylyl, O—($CH_2$)$_n$-phenyl, where n is 0–6, 1- or 2-naphthyl, 2-, 3- or 4-pyridyl, 2- or 3-furanyl or 2- or 3-thienyl,
wherein any of the phenyl, biphenyl, naphthyl, pyridyl, furanyl or thienyl rings may be optionally substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N[($C_1$–$C_6$)-alkyl]$_2$, $SO_2$—$CH_3$, COOH, COO—($C_1$–$C_6$)-alkyl or $CONH_2$;
1,2,3-triazol-5-yl, wherein the triazole ring may be substituted in the 1-, 2- or 3-position by methyl or benzyl; tetrazol-5-yl, where the tetrazole ring may be substituted in the 1- or 2-position by methyl or benzyl;
R2 is H, ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, ($CH_2$)$_n$-furyl, C(O)—($C_1$–$C_6$)-alkyl, C(O)—($C_3$–$C_6$)-cycloalkyl, C(O)—($CH_2$)$_n$-phenyl, C(O)—($CH_2$)$_n$-thienyl, C(O)—($CH_2$)$_n$-pyridyl or C(O)—($CH_2$)$_n$-furyl,
wherein n is 0–5 and in which any of phenyl, thienyl, pyridyl or furyl may be substituted up to two times by Cl, F, CN, $CF_3$, ($C_1$–$C_3$)-alkyl, OH or O—($C_1$–$C_6$)-alkyl;

R3 is H, ($C_1$–$C_6$)-alkyl, F, Cl, Br, CN, $N_3$, O—($C_1$–$C_6$)-alkyl, ($CH_2$)$_n$-phenyl, ($CH_2$)$_n$-thienyl, ($CH_2$)$_n$-pyridyl, ($CH_2$)$_n$-furyl,
wherein is 0–5 and in which any of phenyl, thienyl, pyridyl or furyl may be substituted up to two times by Cl, F, CN, $CF_3$, ($C_1$–$C_3$)-alkyl, OH or O—($C_1$–$C_6$)-alkyl,
($C_2$–$C_6$)-alkynyl, ($C_2$–$C_6$)-alkenyl, OC(O)$CH_3$, ($CH_2$)$_n$—C(O)O($C_1$–$C_6$)-alkyl, ($CH_2$)$_n$—C(O)OH, ($CH_2$)$_n$—C(O)$NH_2$, ($CH_2$)$_n$—C(O)NH$CH_3$ or ($CH_2$)$_n$—C(O)N($CH_3$)$_2$, wherein is 0–3;
R4 is ($C_1$–$C_8$)-alkyl, ($C_3$–$C_7$)-cycloalkyl, ($C_2$–$C_6$)-alkenyl, ($C_2$–$C_6$)-alkynyl, ($C_4$–$C_7$)-cycloalkenyl,
wherein one or more of the hydrogens of the alkyl radicals may be replaced by fluorine or one hydrogen may be replaced by OH, OC(O)$CH_3$, OC(O)H, O—$CH_2$—Ph or O—($C_1$–$C_4$)-alkyl;
($CH_2$)$_n$-pyrrolidin-1-yl, ($CH_2$)$_n$-piperidin-1-yl, ($CH_2$)$_n$-morpholin-4-yl, ($CH_2$)$_n$-piperazin-1-yl, ($CH_2$)$_n$-N-4-methylpiperazin-1-yl, ($CH_2$)$_n$—N-4-benzylpiperazin-1-yl, ($CH_2$)$_n$-phthalimidoyl, where n is 1–6; ($CH_2$)$_n$-aryl or ($CH_2$)$_n$-heteroaryl,
wherein is 0–6 and aryl is phenyl, biphenylyl or 1- or 2-naphthyl and heteroaryl is 2-, 3- or 4-pyridyl, or 2- or 3-thienyl, and the aryl radical or the heteroaryl radical may be optionally substituted up to two times by F, Cl, Br, OH, $CF_3$, O—($C_1$–$C_6$)-alkyl, ($CH_2$)$_n$—$SO_2$—($C_1$–$C_6$)-alkyl, ($CH_2$)$_n$—$SO_2$—$NH_2$, ($CH_2$)$_n$—$SO_2$—N(=CH—N($CH_3$)$_2$), where n is 0–6, NH—$SO_2$—($C_1$–$C_6$)-alkyl, NH—$SO_2$-phenyl,
wherein the phenyl ring may be substituted up to two times by F, Cl, CN, OH, ($C_1$–$C_6$)-alkyl, O—($C_1$–$C_6$)-alkyl, $CF_3$, COOH, COO($C_1$–$C_6$)-alkyl or $CONH_2$;
($C_1$–$C_6$)-alkyl, COOH, COO($C_1$–$C_6$)-alkyl or $CONH_2$; or ($CH_2$)$_n$—A—R8, wherein n is 1–6;
A is O, NH, N—($C_1$–$C_6$)-alkyl, or $SO_2$;
R8 is ($C_1$–$C_8$)-alkyl, ($C_3$–$C_8$)-cycloalkyl,
wherein one or more hydrogens of the alkyl radicals may be replaced by fluorine or one hydrogen may be replaced by OH, OC(O)$CH_3$, OC(O)H, O—$CH_2$—Ph or O—($C_1$–$C_4$)-alkyl;
($CH_2$)$_m$-aryl or ($CH_2$)$_n$-heteroaryl,
wherein m is 0–6 and aryl is phenyl, thienyl or pyridyl and the aryl moiety or the heteroaryl moiety may be optionally substituted up to two times by F, Cl, Br, OH, $CF_3$, O—($C_1$–$C_6$)-alkyl, ($CH_2$)$_n$—$SO_2$—($C_1$–$C_6$)-alkyl, ($CH_2$)$_n$—$SO_2$—$NH_2$, ($CH_2$)$_n$—$SO_2$—N(=CH—N($CH_3$)$_2$), wherein n is 0–6, NH—$SO_2$—($C_1$–$C_6$)-alkyl, NH—$SO_2$-phenyl,
where the phenyl ring may be optionally substituted up to two times by F, Cl, CN, OH, ($C_1$–$C_6$)-alkyl, O—($C_1$–$C_6$)-alkyl, $CF_3$, COOH, COO($C_1$–$C_6$)-alkyl, $CONH_2$, where n is 0–6, COOH, COO($C_1$–$C_6$)-alkyl, or $CONH_2$;
R5 is H;
R6 is Cl, Br, OH, O—($C_1$–$C_6$)-alkyl, O—($CH_2$)$_n$-aryl, or O—($CH_2$)$_n$-heteroaryl,
wherein n is 0–6 and aryl is phenyl and heteroaryl is 2-, 3- or 4-pyridyl or 2- or 3-thienyl;
O—C(O)—H, O—C(O)—($C_1$–$C_6$)-alkyl, O—C(O)—($C_3$–$C_8$)-cycloalkyl, O—C(O)-aryl, O—C(O)-heteroaryl,
wherein aryl is phenyl and heteroaryl is pyridyl, thienyl or furanyl; O-alpha- or -beta-glucuronic acid, SH, S—($C_1$–$C_6$)-alkyl, S—($CH_2$)$_n$-phenyl, wherein n is 0–6, S—C(O)—($C_1$–$C_6$)-alkyl, S—C(O)—($C_3$–$C_8$)- cycloalkyl, S—C(O)-phenyl; SO—($C_1$–$C_6$)-alkyl, SO—$(CH_2)_n$-phenyl, wherein n is 0–6, $SO_2$—($C_1$–$C_6$)-alkyl, $SO_2$—$(CH_2)_n$-phenyl, wherein n is 0–6, $NH_2$, NH—($C_1$–$C_6$)-alkyl, NH—($C_3$–$C_7$)-cycloalkyl, N[($C_1$–$C_6$)-alkyl]$_2$, morpholin-4-yl, pyrrolidin-1-yl, piperidin-1-yl, piperazin-1-yl, 1-methylpiperazin-4-yl, 1-benzylpiperazin-4-yl, NH-phenyl, NH—$CH_2$-phenyl, NH—C(O)—($C_1$–$C_6$)-alkyl or NH—C(O)-phenyl, or R5 and R6 together form =O, wherein n is 2–6, ($C_1$–$C_6$)-alkyl ($C_1$–$C_6$)-alkyl, $CH_2$-phenyl $CH_2$-phenyl, $H_3C$ $CH_3$ or =NOH, and their physiologically acceptable salts and physiologically functional derivatives.

In a particularly preferred embodiment are compounds of formula I wherein:

R1, R1' are independently selected from H, F, Cl, Br, —OH, O—($C_1$–$C_6$)-alkyl or ($C_1$–$C_6$)-alkyl,
  wherein one of the hydrogens of the alkyl radicals may be replaced by OH;

R2 is H, ($C_1$–$C_6$)-alkyl or C(O)—($C_1$–$C_6$)-alkyl;

R3 is Cl, Br, $(CH_2)_n$-COO($C_1$–$C_6$)-alkyl, $(CH_2)_n$—COOH or $(CH_2)_n$—$CONH_2$,
  wherein n is 0 or 1;

R4 is ($C_1$–$C_4$)-alkyl or ($C_3$–$C_6$)-cycloalkyl, wherein one of the hydrogens of the alkyl radicals may be replaced by OH;

$(CH_2)_n$-aryl or $(CH_2)_n$-heteroaryl,
  wherein n is 0–6 and aryl is phenyl and heteroaryl is 1- or 2-naphthyl, 2-, 3- or 4-pyridyl or 2- or 3-thienyl and the aryl radical or heteroaryl radical may be optionally substituted up to two times by F, Cl, Br, OH, $CF_3$, O—($C_1$–$C_6$)-alkyl, $SO_2$—($C_1$–$C_6$)-alkyl, $(CH_2)_n$—$SO_2$—$NH_2$, where n is 0–6; ($C_1$–$C_6$)-alkyl, COOH, COO($C_1$–$C_6$)-alkyl or $CONH_2$; or $(CH_2)_n$—A—R8, wherein n is 1–6;

A is O or $SO_2$;

R8 is ($C_1$–$C_8$)-alkyl, ($C_3$–$C_8$)-cycloalkyl, wherein one of the hydrogens of the alkyl radicals may be replaced by OH;

$(CH_2)_m$-aryl or $(CH_2)_m$-heteroaryl,
  where m is 0–6 and aryl is phenyl and heteroaryl is thienyl and the aryl moiety or the heteroaryl moiety may be optionally substituted up to two times by F, Cl, Br, OH, $CF_3$, O—($C_1$–$C_6$)-alkyl, $SO_2$—($C_1$–$C_6$)-alkyl, $SO_2$—$NH_2$, COOH, COO($C_1$–$C_6$)-alkyl or $CONH_2$;

R5 is H;

R6 is OH or O—($C_1$–$C_6$)-alkyl, wherein n is 0–6;
  O—C(O)—($C_1$–$C_6$)-alkyl, O—C(O)-aryl, O—C(O)-heteroaryl,
  wherein aryl is phenyl and heteroayl is thienyl;
  O-alpha or -beta-glucuronic acid, $SO_2$—($C_1$–$C_6$)-alkyl, $SO_2$—$(CH_2)_n$-phenyl, where n is 0–6, $NH_2$, morpholin-4-yl, NH—C(O)—($C_1$–$C_6$)-alkyl or NH—C(O)-phenyl or R5 and R6 together form =O, where n is 2–6, and their physiologically acceptable salts.

The invention relates to compounds of formula I, in the form of their racemates, racemic mixtures and pure enantiomers, and to their diastereomers and mixtures thereof.

The alkyl, alkenyl and alkynyl radicals in the substituents R1, R1', R2, R3, R4, R6, R8 and A may be either straight-chain or branched.

Pharmaceutically acceptable salts are particularly suitable for medicinal applications compared with the starting materials or base compounds, due to their higher water solubility. These salts have a pharmaceutically acceptable anion or cation. Suitable pharmaceutically acceptable acid addition salts of the compounds according to the invention are salts of inorganic acids, including but not limited to, hydrochloric acid, hydrobromic acid, phosphoric acid, metaphosphoric acid, nitric acid, sulfonic acid and sulfuric acid, and of organic acids, such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. For medicinal purposes, the chlorine salt, is one of the preferred. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included in the scope of the invention as useful intermediates for the production or purification of pharmaceutically acceptable salts and/or for use in nontherapeutic, for example in-vitro, applications. In addition, pharmaceutically unacceptable anions may be useful for the separation of enantiomers and diastereomers.

The term "physiologically functional derivative" used here relates to any physiologically acceptable derivative of a compound of formula I according to the invention, for example an ester, which on administration to a mammal, such as, for example, man, is able (directly or indirectly) to form a compound of formula I or an active metabolite thereof.

The physiologically functional derivatives also include prodrugs of the compounds according to the invention. Such prodrugs are able to be metabolized in vivo to a compound according to the invention. These prodrugs may be active or inactive.

The compounds according to the invention may also be present in various polymorphic forms, for example as amorphous and crystalline polymorphic forms. All polymorphic forms of the compounds according to the invention are included in the scope of the invention and are a further aspect of the invention.

Hereinbelow, all references to "compound(s) according to formula (I)" refer to compound(s) of formula (I) as described above, and to their salts, solvates and physiologically functional derivatives as described herein.

The amount of a compound according to formula (I) which is necessary in order to achieve the desired biological effect is dependent on a number of factors, for example the specific compound selected, the intended use, the manner of administration and the clinical condition of the patient. In general, the daily dose is in the range from 0.3 mg to 100 mg (typically from 3 mg to 50 mg) per day per kilogram of body weight, for example 3-10 mg/kg/day. An intravenous dose may be, for example, in the range from 0.3 mg to 1.0 mg/kg, which may be suitably administered as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampoules for injection may contain, for example, from 1 mg to 100 mg, and orally administrable individual dose formulations, such as, for example, tablets or capsules, may contain, for example, from 1.0 to 1000 mg, typically from 10 to 600 mg. In the case of pharmaceutically acceptable salts, the abovementioned weight details relate to the weight of the dihydrothiazolium ion derived from the salt. For the prophylaxis or therapy of the abovementioned conditions, the compounds according to formula (I) may be used themselves as the compound, but they are also present in the form of a pharmaceutical composition with a tolerable excipient. The excipient is a pharmaceutically aceptable excipient, this means that it is compatible with the other constituents of the composition and is not harmful to the patient's health. The excipient may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions according to the invention may be prepared by one of the known pharmaceutical methods, which essentially consist in mixing the constituents with pharmacologically acceptable excipients and/or auxiliaries.

Pharmaceutical compositions according to the invention are those which are suitable for oral, rectal, topical, peroral, (e.g. sublingual) and parenteral (e.g. subcutaneous, intramuscular, intradermal or intravenous) administration, although the most suitable manner of administration in each individual case is dependent on the nature and severity of the condition to be treated and on the nature of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be present in separate units, such as, for example, capsules, cachets, lozenges or tablets which in each case contain a certain amount of the compound according to formula (I); as powders or granules; as solution or suspension in an aqueous or nonaqueous liquid; or as an oil-in-water or water-in-oil emulsion. As already mentioned, these compositions may be prepared by any suitable pharmaceutical method which includes a step in which the active compound and the excipient (which may consist of one or more additional constituents) are brought into contact. In general, the compositions are prepared by uniform and homogeneous mixing of the active compound with a liquid and/or finely divided solid excipient, after which the product, if necessary, is shaped. Thus a tablet, for example, may be prepared by pressing or shaping a powder or granules of the compound, if appropriate with one or more additional constituents. Pressed tablets may be prepared by tableting the compound in free-flowing form, such as, for example, a powder or granules, if appropriate mixed with a binder, lubricant, inert diluent and/or one (a number of) surface-active/dispersing agents in a suitable machine. Shaped tablets may be prepared by shaping the pulverulent compound, moistened with an inert liquid diluent, in a suitable machine.

Pharmaceutical compositions which are suitable for peroral (sublingual) administration include lozenges, which contain a compound according to formula (I) with a flavoring, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations of a compound according to formula (I), which are preferably isotonic with the blood of the intended recipient. These preparations are preferably administered intravenously, although the administration may also take place subcutaneously, intramuscularly or intradermally as an injection. These preparations may be prepared by mixing the compound with water and rendering the obtained solution sterile and isotonic with the blood. Injectable compositions according to the invention in general contain from 0.1 to 5% by weight of the active compound.

Suitable pharmaceutical compositions for rectal administration are preferably present as individual dose suppositories. These may be prepared by mixing a compound according to formula (I) with one or more conventional solid excipients, for example cocoa butter, and shaping the resulting mixture.

Suitable pharmaceutical compositions for topical application to the skin are preferably present as ointment, cream, lotion, paste, spray, aerosol or oil. Excipients which may be used are petroleum jelly, lanolin, polyethylene glycols, alcohols and combinations of two or more of these substances. The active compound is in general present in a concentration of from 0.1 to 15% by weight of the composition, for example of from 0.5 to 2%.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from about 1% to 35%, preferably from about 3% to 15%. As a particular possibility, the active compound may be released by electrotransport or iontophoresis, as described, for example, in Pharmaceutical Research, 2(6):318 (1986).

The invention furthermore relates to a process for the preparation of the compounds of formula I, the process comprises reactions steps according to the scheme set forth below:

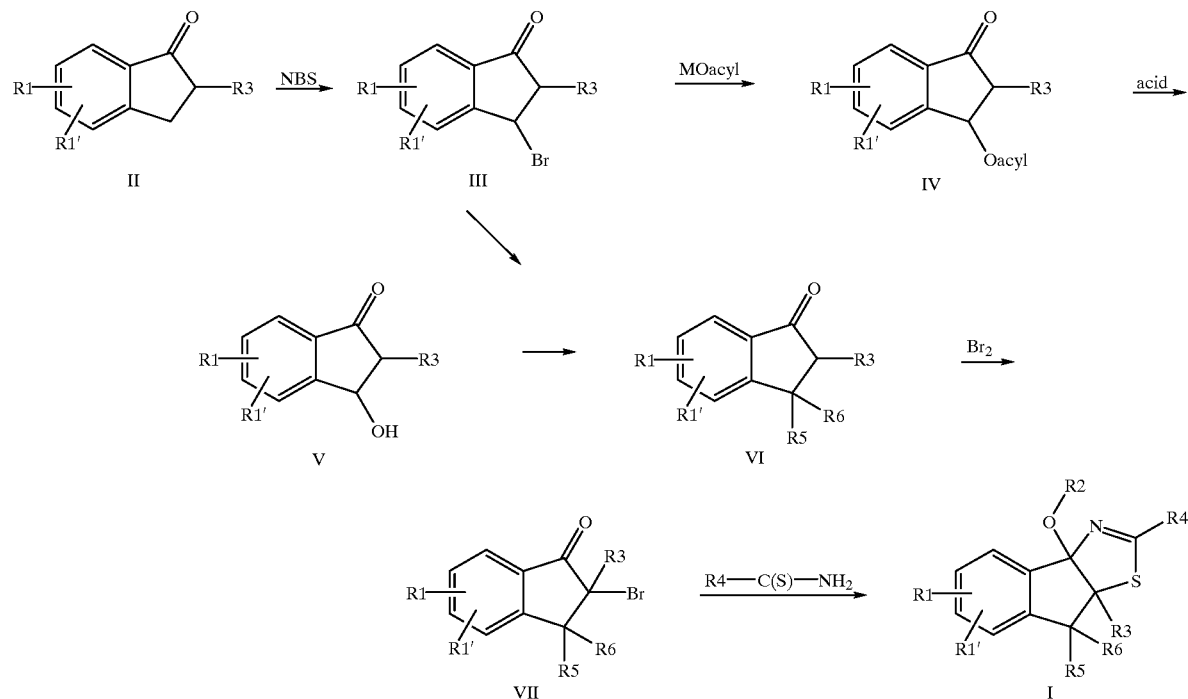

As part of this reaction scheme, compounds of Formula II,

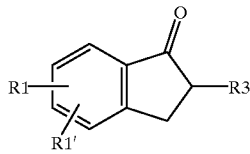

Formula II in which R1, R1' and R3 are as defined above, are converted into a compound of Formula III using N-bromosuccinimide.

The compounds of Formula III are then reacted with metal salts of organic acids (MOacyl), such as, for example, silver acetate, to yield compounds of Formula IV.

Another option is to convert compounds of Formula III by nucleophilic exchange with O-, S- or N-nucleophiles into the corresponding O-, S- or N-substituted compounds of Formula VI in which the radicals R1, R1', R3, R5 and R6 are as defined above.

Compounds of Formula IV may be converted into compounds of Formula V, for example by acid hydrolysis.

Under standard conditions, the compounds of Formulae V and VI may be converted by reaction with bromine into the corresponding alpha-bromoketones of Formula VII, in which, for example, R5 may be hydrogen and R6 may be OH. Reaction of the thioamides of formula R4-C(S)—NH$_2$, in which R4 is as defined above, with compounds of formula VII gives compounds of formula I in which R2 is hydrogen. Using standard methods, these compounds may be converted into compounds of formula I in which R2 is as described further above.

Suitable inorganic acids for salt formation are, for example: hydrohalic acids, such as hydrochloric acid and hydrobromic acid, and also sulfuric acid, phosphoric acid and amidosulfonic acid.

Organic acids which are suitable for salt formation are, for example: formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4 (3H)-one 2,2-dioxide.

In the reaction scheme described above, it is advantageous to react the compounds of Formula VII with the thioamides R4-C(S)—NH$_2$ in a molar ratio of from 1:1 to 1:1.5. The reaction is carried out in an inert solvent, for example in polar organic solvents, such as dimethylformamide, dimethylacetamide, N-methyl-2-pyrrolidone, dimethyl sulfoxide, dioxane, tetrahydrofuran, acetonitrile, nitromethane or diethylene glycol dimethyl ether. Particularly preferred solvents, include but are not limited to methyl acetate and ethyl acetate, short-chain alcohols, such as methanol, ethanol, propanol, isopropanol, and lower dialkyl ketones, such as, for example, acetone, butan-2-one or hexan-2-one. Mixtures of the reaction media mentioned may also be used; and mixtures of the solvents mentioned with solvents which, taken per se, are less suitable, such as, for example, mixtures of methanol with benzene, ethanol with toluene, methanol with diethyl ether or with tert-butyl methyl ether, ethanol with carbon tetrachloride, acetone with chloroform, dichloromethane or 1,2-dichloroethane, may also be used, where the more polar solvent in each case should be used in an excess. The reactants may be suspended or dissolved in the respective reaction medium. In principle, the reactants may also be reacted in the absence of a solvent, in particular if the respective thioamide has a melting point which is as low as possible. The reaction, which proceeds in a slightly exothermic manner, may be carried out between −10° C. and 150° C., preferably between 30° C. and 100° C. A temperature range between 50° C. and 90° C. has generally been found to be favorable.

The reaction time is largely dependent on the reaction temperature and is between 2 minutes and 3 days at relatively high and relatively low temperatures, respectively. In the favorable temperature range, the reaction time is generally between 5 minutes and 48 hours. In the course of the reaction, the compounds of Formula I frequently form a poorly soluble deposit in the form of their acid addition salts, addition of a suitable precipitating agent is subsequently added. Those precipitating agents used are, for example, hydrocarbons such as benzene, toluene, cyclohexane or heptane or carbon tetrachloride; in particular, alkyl acetates, such as ethyl acetate or n-butyl acetate, or dialkyl ethers, such as diethyl ether, diisopropyl ether, di-n-butyl ether or tert-butyl methyl ether prove particularly suitable. If the reaction mixture remains in solution after the end of the reaction, the salts of the compounds of Formula I may be precipitated using one of the precipitating agents mentioned, if appropriate after concentration of the reaction solution. Furthermore, the solution of the reaction mixture may also be advantageously filtered into the solution of one of the precipitating agents mentioned, with stirring. Work-up of the reaction mixture may also be carried out such that the reaction mixture is rendered alkaline by addition of an organic base, such as, for example, triethylamine or diisobutylamine or ammonia or morpholine or piperidine or 1,8-diazabicyclo[5.4.0]undec-7-ene, and the crude reaction product is purified by chromatography, for example on a silica gel column, after concentration (e.g., by vacuum). Suitable eluents for the chromatography are, for example, mixtures of ethyl acetate with methanol, mixtures of dichloromethane with methanol, mixtures of toluene with methanol or ethyl acetate or mixtures of ethyl acetate with hydrocarbons such as heptane. If the purification of the crude product is carried out in the manner previously described, an acid addition product of Formula I may be obtained from the pure base of the compound of formula I thus obtained by dissolving or suspending the base in an organic protic solvent, such as methanol, ethanol, propanol or isopropanol, or in an organic aprotic solvent, such as ethyl acetate, diethyl ether, diisopropyl ether, tert-butyl methyl ether, dioxane, tetrahydrofuran, acetone or butan-2-one, and then treating this mixture with at least an equimolar amount of an inorganic acid such as, for example, hydrochloric acid, dissolved in an inert solvent such as, for example, diethyl ether or ethanol, or another of the inorganic or organic acids mentioned further above.

The compounds of formula I may be recrystallized from an inert suitable solvent such as, for example, acetone, butan-2-one, acetonitrile or nitromethane. However, particularly preferred is reprecipitation from a solvent such as, for example, dimethylformamide, dimethylacetamide, nitromethane, acetonitrile, preferably methanol or ethanol.

The reaction of the compounds of formula VII with the thioamides R4-C(S)—NH$_2$ may also be carried out such that at least an equimolar amount of a base, such as, for example, triethylamine, is added to the reaction mixture and the resulting free bases of Formula I are then optionally converted into their acid addition products.

The acid addition products of the compounds of Formula I may be reacted to give the free bases of Formula I by treatment with bases. Suitable bases are, for example, solutions of inorganic hydroxides, such as lithium hydroxide, sodium hydroxide, potassium hydroxide, calcium hydroxide or barium hydroxide, carbonates or hydrogen carbonates, such as sodium carbonate or potassium carbonate, sodium hydrogen carbonate or potassium hydrogen carbonate, ammonia and amines, such as triethylamine, diisopropylamine, dicyclohexylamine, piperidine, morpholine, methyldicyclohexylamine.

Thioamides of formula R4-C(S)—NH$_2$ are either commercially available or may be obtained, for example, by reaction of the corresponding carboxamide with phosphorus pentasulfide in pyridine (R. N. Hurd, G. Delameter, Chem. Rev. 61, 45 (1961)), or with Lawesson's reagent in toluene, pyridine, hexamethylphosphoric triamide [Scheibye, Pedersen and Lawesson: Bull. Soc. Chim. Belges 87, 229 (1978)], preferably in a mixture of tetrahydrofuran with 1,3-dimethyl-3,4,5,6-tetrahydro-2(1H)-pyrimidinone or 1,3-dimethyl-2-imidazolidinone. Hydroxyl, amino or additional carbonyl functions are in this case protected using a removable protective function, such as, for example, a benzyl, tert-butyloxycarbonyl or benzyloxycarbonyl radical, or converted into an optionally cyclic acetal. Methods for this are described, for example, in Th. W. Greene and P. G. M. Wuts, Protective Groups in Organic Synthesis, Second Edition, 1991, John Wiley & Sons, New York.

Thioamides of formula R4-C(S)—NH$_2$ may also be obtained by reacting nitriles of formula R4-CN with hydrogen sulfide (Houben-Weyl IX, 762) or thioacetamide (E. C. Taylor, J. A. Zoltewicz, J. Am. Chem. Soc. 82, 2656 (1960)) or O,O-diethyl dithiophosphoric acid. The reactions with hydrogen sulfide are preferably carried out in an organic solvent, such as methanol or ethanol, those with thioacetamide in a solvent such as dimethylformamide with addition of hydrochloric acid, and those with O,O-diethyl dithiophosphoric acid in a solvent such as ethyl acetate under acidic, e.g. HCl, conditions at room temperature or with warming.

The examples given below serve to illustrate the invention, but without restricting it. The measured melting or decomposition points (m.p.) were not corrected and are generally dependent on the heating rate.

TABLE 1

Examples

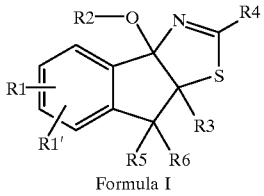

Formula I

| Example | R1; R' | R2 | R3 | R4 | R5 | R6 | Salt | m.p.[° C.] |
|---|---|---|---|---|---|---|---|---|
| 1 | 6-Cl; H | H | H | Phenyl | H | OH | — | 152 |
| 2 | H; H | H | H | phenyl-2-OH | H | OH | — | 110 (decomp.) |

The compounds of formula I are distinguished by favorable effects on lipid metabolism; in particular, they are suitable as anorectics. Other favorable effects on lipid metabolism include lowering cholesterol or low density lipoproteins (LDL) and increasing high density lipoproteins (HDL). The compounds may be employed on their own or in combination with other anorectically active compounds. Such further anorectically active compounds are mentioned, for example, in the Rote Liste, chapter 01 under slimming preparations/anorectics. Examples include, but are not limited to, DECORPA© (from Pierre Fabre Pharma, common name, *sterculia*), XENICAL© (from Roche, common name *orlistat*), ANTIADIPOSITUM X-112S (from Haenseler, common name, D-norpseudoephedrin-HCl), FASUPOND© (from Eu Rho Arzneil, common name, D-norpseudoephedrin-HCl), MIRAPRONT© N (from Mack, Illert., common name, D-norpseudoephedrin-Poly (styrol, divinylbenzol) sulfonate), REGENON© 1-retard (from Temmler Pharma, common name, Amfepramon-HCl), RONDIMEN© D (from ASTA Medica AWD, common name, Mefenorex-HCl), TENUATE© Retard (from Artegodan, common name, Amfepramon-HCl), Vita-Schlanktropfen Schuck (from Schuck, common name, D-norpseudoephedrin-HCl), VENCIPON© N (from Artesan, common name, Ephedrin-HCl), CEFAMADAR© (from Cefak, common name Madar D4), and Helianthus tuberosus (Plantina). The compounds are suitable for the prophylaxis and in particular for the treatment of obesity. The compounds are furthermore suitable for the prophylaxis and in particular for the treatment of type II diabetes.

The efficacy of the compounds was tested as follows:

Biological test model:

The anorectic action was tested on female NMRI mice. After withdrawal of food for 24 hours, a test preparation of the invention was administered via a stomach tube. Kept individually and with free access to drinking water, the animals were offered evaporated milk 30 minutes after the administration of the preparation. The consumption of evaporated milk was determined half-hourly for 1.5 hours and the general condition of the animals was observed. The measured milk consumption was compared with that of untreated control animals.

TABLE 2

Anorectic action, measured as reduction of the cumulated milk consumption of treated animals compared to untreated animals.

Compound/Example

| Formula | Oral dose [mg/kg] | Number of animals/ cumulated milk consumption of the treated animals N/[ml] | Number of animals/ cumulated milk consumption of the untreated control animals N/[ml] | Reduction of the cumulated milk consumption in % of the control |
|---|---|---|---|---|
| Example 1 | 30 | 5/1.06 | 5/1.54 | 31% |

The data in the above table indicate that the compounds of formula I exhibit very good anorectic action. The preparation of some examples is described in detail below; the other compounds of formula I were obtained in a similar manner:

EXAMPLE 1

(Compound 1)

6-Chloro-2-phenyl-8,8a-dihydroindeno[1,2-d]thiazole-3a,8-diol:

a) 3-Bromo-5-chloroindan-1-one:

8.33 g (50 mmol) of 5-chloroindan-1-one and 8.9 g (50 mmol) of N-bromosuccinimide were suspended in 175 ml of carbon tetrachloride, admixed with 1 g of benzoyl peroxide and, with stirring, heated under reflux for 3 h. The cooled reaction solution was filtered, extracted 2× with 100 ml of water, dried over magnesium sulfate, filtered and concentrated under reduced pressure. The residue was dissolved in 120 ml of a 1:1 mixture of hot n-heptane and cyclohexane, boiled with activated carbon and filtered, and the filtrate was concentrated under reduced pressure. This gave 3-bromo-5-chloroindan-1-one having a melting point of 96–97° C.

b) 3-Acetoxy-5-chloroindan-1-one:

4.91 g (20 mmol) of 3-bromo-5-chloroindan-1-one and 3.34 g (20 mmol) of silver acetate were suspended in 100 ml of acetic acid and, with stirring, and heated under reflux for 5 h. The cooled reaction solution was concentrated under reduced pressure and the residue was purified by chromatography on silica gel using toluene/acetone 10/1. This gave 3-acetoxy-5-chloroindan-1-one of melting point 65–67° C.

c) 5-Chloro-3-hydroxyindan-1-one:

With addition of 50 ml of 3N HCl, 1.98 g (8.8 mmol) of 3-acetoxy-5-chloroindan-1-one were dissolved in 10 ml of acetonitrile. The reaction mixture was stirred at room temperature for 48 h. The solvent acetonitrile was then distilled off under reduced pressure and the precipitated crude product was filtered off and purified by chromatography on silica gel using toluene/acetone 5/1. The product, 5-chloro-3-hydroxyindan-1-one, had a melting point of 125–128° C.

d) 2-Bromo-5-chloro-3-hydroxyindan-1-one:

0.69 g (3.78 mmol) of 5-chloro-3-hydroxyindan-1-one was dissolved in 100 ml of diethyl ether; 1 drop of bromine was added with stirring, and the mixture was stirred until the color had disappeared. The mixture was then cooled to −5° C., and 0.194 ml (3.78 mmol) of bromine in 2 ml of dichloromethane was added dropwise over a period of 30 min. Stirring was then continued for 30 min, 50 ml of water was added and the organic phase was separated off, dried over magnesium sulfate and filtered. The filtrate was concentrated under reduced pressure and the residue was dried under reduced pressure. This gave 2-bromo-5-chloro-3-hydroxyindan-1-one having a melting point of 118–119° C.

e) 6-Chloro-2-phenyl-8,8a-dihydroindeno[1,2-d]thiazole-3a,8-diol:

0.6 g (2.3 mmol) of 2-bromo-5-chloro-3-hydroxyindan-1-one and 0.473 g (3.45 mmol) of thiobenzamide were dissolved in 5 ml of isopropanol. 0.478 ml (3.45 mmol) of triethylamine was added, and the mixture was then stirred at room temperature for 12 h and subsequently at 50° C. for 8 h. The cooled reaction mixture was concentrated under reduced pressure and the residue was purified by chromatography on silica gel by initially using n-heptane/ethyl acetate 3/1 and then toluene/acetone 5/1. This gave 6-chloro-2-phenyl-8,8a-dihydroindeno[1,2-d]thiazole-3a,8-diol having a melting point of 151–153° C. (with decomposition).

What is claimed is:
1. A compound of formula (I):

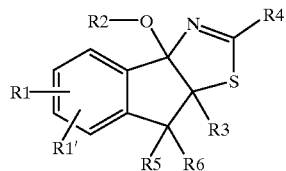

in which
R1, R1' are independently selected from H, F, Cl, Br, I, CF$_3$, NO$_2$, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O-(C$_1$–C$_6$)-alkyl,
   wherein one or more of the hydrogens of the alkyl, alkenyl, or alkynyl radicals may be replaced by fluorine, or one hydrogen may be replaced by OH, OC(O)CH$_3$, OC(O)H, O—CH$_2$—Ph, NH$_2$, NH—CO—CH$_3$ or N(COOCH$_2$Ph)$_2$;

SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-phenyl, SO—(C$_1$–C$_6$)-alkyl, SO—(CH$_2$)$_n$-phenyl, SO$_2$—(C$_1$–C$_6$)-alkyl, SO$_2$—(CH$_2$)$_n$-phenyl,
   wherein n is 0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl or NH$_2$;

NH$_2$, NH—(C$_1$–C$_6$)-alkyl, N[(C$_1$–C$_6$)-alkyl]$_2$, NH(C$_1$–C$_7$)-acyl, phenyl, biphenylyl, O—(CH$_2$)$_n$-phenyl, where n is 0–6, 1- or 2-naphthyl, 2-, 3- or 4-pyridyl, 2- or 3-furanyl or 2- or 3-thienyl,
   wherein any of the phenyl, biphenyl, naphthyl, pyridyl, furanyl or thienyl rings may be optionally substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N[(C$_1$–C$_6$)-alkyl]$_2$, SO$_2$—CH$_3$, COOH, COO—(C$_1$–C$_6$)-alkyl or CONH$_2$;

1,2,3-triazol-5-yl, wherein the triazole ring may be substituted in the 1-, 2- or 3-position by methyl or benzyl; tetrazol-5-yl, where the tetrazole ring may be substituted in the 1 - or 2-position by methyl or benzyl; 1,3,4-oxadiazol-2-yl; 2-amino-1,3,4-oxadiazol-5-yl,
   wherein the amino function may be mono- or disubstituted by (C$_1$–C$_6$)-alkyl, —C(O)—(C$_1$–C$_6$)-alkyl, —C(O)—(cyclo-C$_3$–C$_7$)-alkyl, —C(O)-phenyl, —C(O)—NH—(C$_1$–C$_6$)-alkyl, —C(O)—NH—(cyclo-C$_3$–C$_7$)-alkyl, or —C(O)—NH-aryl, wherein aryl is phenyl, 2-, 3- or 4-pyridyl, 2- or 3-thienyl or 2- or 3-furanyl, —C(O)-morpholin-4-yl, —C(O)-piperidin-1-yl, —C(O)-piperazin-4-yl, —C(O)—1-methyl-, 1-benzyl-piperazin-4-yl, —SO$_2$—(C$_1$–C$_6$)-alkyl or —SO$_2$-phenyl,
   wherein the phenyl ring may be substituted up to two times by F, Cl, Br, CN, CF$_3$, OH, OCF$_3$, (C$_1$–C$_6$)-alkyl, O—(C$_1$–C$_6$)-alkyl, (CH$_2$)$_n$-phenyl, O—(CH$_2$)$_n$-phenyl, where n is 0–6, NH$_2$, NH(C$_1$–C$_6$)-alkyl, N[(C$_1$–C$_6$)-alkyl]$_2$, SO$_2$—CH$_3$, COOH, COO—(C$_1$–C$_6$)-alkyl or CONH$_2$;

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(C$_1$–C$_6$)-alkyl, C(O)—(C$_3$–C$_6$)-cycloalkyl, C(O)—(CH$_2$)$_n$-phenyl, C(O)—(CH$_2$)$_n$-thienyl, C(O)—(CH$_2$)$_n$-pyridyl or C(O)—(CH$_2$)$_n$-furyl,
   wherein n is 0–5 and in which any of phenyl, thienyl, pyridyl or furyl may be optionally substituted up to two times by Cl, F, CN, CF$_3$, (C$_1$–C$_3$)-alkyl, OH or O—(C$_1$–C$_6$)-alkyl;

R3 is H, (C$_1$–C$_6$)-alkyl, F, Cl, Br, CN, N$_3$, O—(C$_1$–C$_6$)-alkyl, (CH$_2$)$_n$-phenyl, (CH$_2$)$_n$-thienyl, (CH$_2$)$_n$-pyridyl, (CH$_2$)$_n$-furyl,
   where n is 0–5 and in which any of phenyl, thienyl, pyridyl or furyl may be optionally substituted up to two times by Cl, F, CN, CF$_3$, (C$_1$–C$_3$)-alkyl, OH or O—(C$_1$–C$_6$)-alkyl, (C$_2$–C$_6$)-alkynyl, (C$_2$–C$_6$)-alkenyl, OC(O)CH$_3$, (CH$_2$)$_n$—C(O)O(C$_1$–C$_6$)-alkyl, (CH$_2$)$_n$—C(O)OH, (CH$_2$)$_n$—C(O)NH$_2$, (CH$_2$)$_n$—C(O)NHCH$_3$ or (CH$_2$)$_n$—C(O)N(CH$_3$)$_2$, where n is 0–3;

R4 is (C$_1$–C$_8$)-alkyl, (C$_3$–C$_7$)-cycloalkyl, (C$_2$–C$_6$)-alkenyl, (C$_2$–C$_6$)-alkynyl, (C$_4$–C$_7$)-cycloalkenyl,
   wherein one or more of the hydrogens of the alkyl radicals may be replaced by fluorine or one hydrogen may be replaced by OH, OC(O)CH$_3$, OC(O)H, O—CH$_2$—Ph or O—(C$_1$–C$_4$)-alkyl; is (CH$_2$)$_n$-pyrrolidin-1-yl, (CH$_2$)$_n$-piperidin-1-yl, (CH$_2$)$_n$-morpholin-4-yl, (CH$_2$)$_n$-piperazin-1-yl, (CH$_2$)$_n$-N-4-methylpiperazin-1-yl, (CH$_2$)$_n$—N-4-benzylpiperazin-1-yl, (CH$_2$)$_n$-phthalimidoyl, where n is 1–6;

(CH$_2$)$_n$-aryl or (CH$_2$)$_n$-heteroaryl,
   where n is 0–6 and aryl is phenyl, biphenylyl or 1 - or 2-naphthyl and heteroaryl is 2-, 3- or 4-pyridyl, 2- or 3-thienyl, 2- or 3-furyl, 2-, 4- or 5-thiazolyl, 2-, 4- or 5-oxazolyl, 1-pyrazolyl, 3- or 5-isoxazolyl, 2- or 3-pyrrolyl, 2- or 3-pyridazinyl, 2-, 4- or 5-pyrimidinyl, 2-pyrazinyl, 2-(1,3,5-triazinyl), 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl,
   wherein the aryl radical or the heteroaryl radical may be optionally substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, (CH$_2$)$_n$—SO$_2$—(C$_1$–C$_6$)-alkyl, (CH$_2$)$_n$—SO$_2$—NH$_2$, (CH$_2$)$_n$—SO$_2$—N(=CH—N(CH$_3$)$_2$), wherein n is 0–6, (C$_1$–C$_6$)-alkyl, (C$_3$–C$_6$)-cycloalkyl, COOH, COO(C$_1$–C$_6$)-alkyl, COO(C$_3$–C$_6$)-cycloalkyl, CONH$_2$, CONH(C$_1$–C$_6$)-alkyl, CON[(C$_1$–C$_6$)-alkyl]$_2$, CONH(C$_3$–C$_6$)-cycloalkyl, NH$_2$, NH—CO—(C$_1$–C$_6$)-alkyl, NH—CO-phenyl, NH—SO$_2$-(C$_1$–C$_6$)-alkyl, NH—SO$_2$-phenyl,
      wherein the phenyl ring may be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl or CONH$_2$;
   pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl or SO$_2$—(CH$_2$)$_n$-phenyl, wherein n is 0–3;

(CH$_2$)$_n$—A—R8, wherein n is 1–6;
A is O, NH, N—(C$_1$–C$_6$)-alkyl, NCHO, N(CO—CH$_3$), S, SO or SO$_2$;
R8 is (C$_1$–C$_8$)-alkyl, (C$_3$–C$_8$)-cycloalkyl,
   wherein one or more hydrogens of the alkyl radicals may be replaced by fluorine or one hydrogen may be replaced by OH, OC(O)CH$_3$, OC(O)H, O—CH$_2$—Ph or O—(C$_1$–C$_4$)-alkyl; is (CH$_2$)$_m$-aryl, wherein m is 0–6 and aryl is phenyl, thienyl or pyridyl and the aryl moiety may be optionally substituted up to two times by F, Cl, Br, OH, $CF_3$, $NO_2$, CN, $OCF_3$, O—$(C_1-C_6)$-alkyl, S—$(C_1-C_6)$-alkyl, SO—$(C_1-C_6)$-alkyl, $(CH_2)_n$—$SO_2$—$(C_1-C_6)$-alkyl, $(CH_2)_n$—$SO_2$—$NH_2$, $(CH_2)_n$—$SO_2$—N(=CH—N($CH_3$)$_2$), $(CH_2)_n$—$SO_2$—NH$(C_1-C_8)$-alkyl, $(CH_2)_n$—$SO_2$—N[$(C_1-C_8)$-alkyl]$_2$, $(CH_2)_n$—$SO_2$—NH$(C_3-C_8)$-cycloalkyl, $(CH_2)_n$—$SO_2$—N[$(C_3-C_8)$-cycloalkyl$_2$], where n is 0–6, $(C_1-C_6)$-alkyl, $(C_3-C_6)$-cycloalkyl, COOH, COO$(C_1-C_6)$-alkyl, COO$(C_3-C_6)$-cycloalkyl, $CONH_2$, CONH$(C_1-C_6)$-alkyl, CON[$(C_1-C_6)$-alkyl]$_2$, CONH$(C_3-C_6)$-cycloalkyl, $NH_2$, NH$(C_1-C_6)$-alkyl, N[$(C_1-C_6)$-alkyl]$_2$, NH—CO—$(C_1-C_6)$-alkyl, NH—CO-phenyl, NH—$SO_2$-phenyl, where the phenyl ring may be optionally substituted up to two times by F, Cl, CN, OH, $(C_1-C_6)$-alkyl, O—$(C_1-C_6)$-alkyl, $CF_3$, COOH, COO$(C_1-C_6)$-alkyl or $CONH_2$;

NH—$SO_2$—$(C_1-C_8)$-alkyl, N$(C_1-C_6)$-alkyl-$SO_2$—$(C_1-C_8)$-alkyl, pyrrolidin-1-yl, morpholin-1-yl, piperidin-1-yl, piperazin-1-yl, 4-methylpiperazin-1-yl, $(CH_2)_p$-phenyl, O—$(CH_2)_p$-phenyl, S—$(CH_2)_p$-phenyl or $SO_2$—$(CH_2)_p$-phenyl, wherein p is 0–3;

R5 is H;

R6 is Cl, Br, OH, O—$(C_1-C_6)$-alkyl, O—$(CH_2)_n$-aryl, O—$(CH_2)_n$-heteroaryl
wherein n is 0–6 and aryl is phenyl and heteroaryl is 2-, 3- or 4-pyridyl or 2- or 3-thienyl;

O—C(O)—H, O—C(O)—$(C_1-C_6)$-alkyl, O—C(O)—$(C_3-C_8)$-cycloalkyl, O—C(O)-aryl, O—C(O)-heteroaryl,
wherein aryl is phenyl and heteroaryl is pyridyl, thienyl or furanyl;

O-alpha- or -beta-glucuronic acid, SH, S—$(C_1-C_6)$-alkyl, S—$(CH_2)_n$-phenyl, wherein n is 0–6, S—C(O)—$(C_1-C_6)$-alkyl, S—C(O)—$(C_3-C_8)$-cycloalkyl, S—C(O)-phenyl; SO—$(C_1-C_6)$-alkyl, SO—$(CH_2)_n$-phenyl, wherein n is 0–6, $SO_2$—$(C_1-C_6)$-alkyl, $SO_2$—$(CH_2)_n$-phenyl, wherein n is 0–6, $NH_2$, NH—$(C_1-C_6)$-alkyl, NH—$(C_3-C_7)$-cycloalkyl, N[$(C_1-C_6)$-alkyl]$_2$, morpholin-4-yl, pyrrolidin-1-yl, piperidin-1-yl, piperazin-1-yl, 1-methylpiperazin-4-yl, 1-benzylpiperazin-4-yl, NH-phenyl, NH—$CH_2$-phenyl, NH—C(O)—$(C_1-C_6)$-alkyl or NH—C(O)-phenyl;

or

R5 and R6 together form =O, 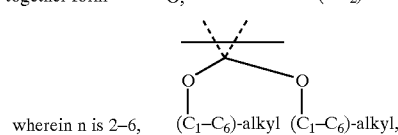

wherein n is 2–6, $(C_1-C_6)$-alkyl $(C_1-C_6)$-alkyl,

-continued

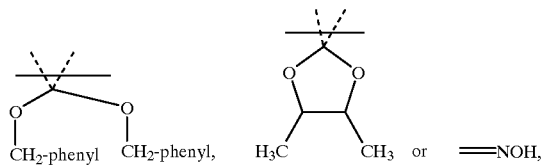

$CH_2$-phenyl $CH_2$-phenyl, $H_3C$ $CH_3$ or =NOH, and their physiologically acceptable salts and physiologically functional derivatives.

2. The compound of claim 1, wherein
R1, R1' are independently selected from H, F, Cl, Br, I, $CF_3$, $NO_2$, CN, COOH, COO$(C_1-C_6)$-alkyl, $CONH_2$, CONH$(C_1-C_6)$-alkyl, CON[$(C_1-C_6)$-alkyl]$_2$, $(C_1-C_6)$-alkyl, $(C_2-C_6)$-alkenyl, $(C_2-C_6)$-alkynyl, O-$(C_1-C_6)$-alkyl,
wherein one or more hydrogens of the alkyl radicals may be replaced by fluorine, or one hydrogen may be replaced by OH, OC(O)$CH_3$, OC(O)H, O—$CH_2$—Ph, $NH_2$, NH—CO—$CH_3$ or N(COO$CH_2$Ph)$_2$;

$SO_2$—$NH_2$, $SO_2$NH$(C_1-C_6)$-alkyl, $SO_2$N[$(C_1-C_6)$-alkyl]$_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl, $SO_2$—$(CH_2)_n$-phenyl,
wherein n is 0–6 and the phenyl radical may be optionally substituted up to two times by F, Cl, Br, OH, $CF_3$, $NO_2$, CN, $OCF_3$, O—$(C_1-C_6)$-alkyl, $(C_1-C_6)$-alkyl or $NH_2$;

$NH_2$, NH—$(C_1-C_6)$-alkyl, N[$(C_1-C_6)$-alkyl]$_2$, NH$(C_1-C_7)$-acyl, phenyl, biphenylyl, O—$(CH_2)_n$-phenyl, where n is 0–6, 1- or 2-naphthyl, 2-, 3- or 4-pyridyl, 2- or 3-furanyl or 2- or 3-thienyl,
wherein any of the phenyl, biphenyl, naphthyl, pyridyl, furanyl or thienyl rings may be optionally substituted one to 3 times by F, Cl, Br, I, OH, $CF_3$, $NO_2$, CN, $OCF_3$, O—$(C_1-C_6)$-alkyl, $(C_1-C_6)$-alkyl, $NH_2$, NH$(C_1-C_6)$-alkyl, N[$(C_1-C_6)$-alkyl]$_2$, $SO_2$—$CH_3$, COOH, COO—$(C_1-C_6)$-alkyl or $CONH_2$;

1,2,3-triazol-5-yl, wherein the triazole ring may be substituted in the 1-, 2- or 3-position by methyl or benzyl; tetrazol-5-yl, where the tetrazole ring may be substituted in the 1 - or 2-position by methyl or benzyl;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(C_1-C_6)$-alkyl, C(O)—$(C_3-C_6)$-cycloalkyl, C(O)—$(CH_2)_n$-phenyl, C(O)—$(CH_2)_n$-thienyl, C(O)—$(CH_2)_n$-pyridyl or C(O)—$(CH_2)_n$-furyl,
wherein n is 0–5 and in which any of phenyl, thienyl, pyridyl or furyl may be substituted up to two times by Cl, F, CN, $CF_3$, $(C_1-C_3)$-alkyl, OH or O—$(C_1-C_6)$-alkyl;

R3 is H, $(C_1-C_6)$-alkyl, F, Cl, Br, CN, $N_3$, O—$(C_1-C_6)$-alkyl, $(CH_2)_n$-phenyl, $(CH_2)_n$-thienyl, $(CH_2)_n$-pyridyl, $(CH_2)_n$-furyl,
wherein n is 0–5 and in which any of phenyl, thienyl, pyridyl and furyl may be substituted up to two times by Cl, F, CN, $CF_3$, $(C_1-C_3)$-alkyl, OH or O—$(C_1-C_6)$-alkyl, $(C_2-C_6)$-alkynyl, $(C_2-C_6)$-alkenyl, OC(O)$CH_3$, $(CH_2)_n$—C(O)O$(C_1-C_6)$-alkyl, $(CH_2)_n$—C(O)OH, $(CH_2)_n$—C(O)$NH_2$, $(CH_2)_n$—C(O)NH$CH_3$ or $(CH_2)_n$C(O)N$(CH_3)_2$, wherein n is 0–3;

R4 is $(C_1-C_8)$-alkyl, $(C_3-C_7)$-cycloalkyl, $(C_2-C_6)$-alkenyl, $(C_2-C_6)$-alkynyl, $(C_4-C_7)$-cycloalkenyl,
wherein one or more of the hydrogens of the alkyl radicals may be replaced by fluorine or one hydrogen may be replaced by OH, OC(O)CH$_3$, OC(O)H, O—CH$_2$—Ph or O—(C$_1$–C$_4$)-alkyl;

(CH$_2$)$_n$-pyrrolidin-1-yl, (CH$_2$)$_n$-piperidin-1-yl, (CH$_2$)$_n$-morpholin-4-yl, (CH$_2$)$_n$-piperazin-1-yl, (CH$_2$)$_n$-N-4-methylpiperazin-1-yl, (CH$_2$)$_n$—N-4-benzylpiperazin-1-yl, (CH$_2$)$_n$-phthalimidoyl, where n is 1–6; (CH$_2$)$_n$-aryl or (CH$_2$)$_n$-heteroaryl, wherein n is 0–6 and aryl is phenyl, biphenylyl or 1- or 2-naphthyl and heteroaryl is 2-, 3- or 4-pyridyl, or 2- or 3-thienyl, and the aryl radical or the heteroaryl radical may be optionally substituted up to two times by F, Cl, Br, OH, CF$_3$, O—(C$_1$–C$_6$)-alkyl, (CH$_2$)$_n$—SO$_2$—(C$_1$–C$_6$)-alkyl, (CH$_2$)$_n$—SO$_2$—NH$_2$, (CH$_2$)$_n$—SO$_2$—N(=CH—N(CH$_3$)$_2$), where n is 0–6, NH—SO$_2$-(C$_1$–C$_6$)-alkyl, NH—SO$_2$-phenyl, wherein the phenyl ring may be substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl or CONH$_2$;

(C$_1$–C$_6$)-alkyl, COOH, COO(C$_1$–C$_6$)-alkyl or CONH$_2$; or (CH$_2$)$_n$—A—R8, wherein n is 1–6;

A is O, NH, (C$_1$–C$_6$)-alkyl, or SO$_2$;

R8 is (C$_1$–C$_8$)-alkyl, (C$_3$–C$_8$)-cycloalkyl, wherein one or more hydrogens of the alkyl radicals may be replaced by fluorine or one hydrogen may be replaced by OH, OC(O)CH$_3$, OC(O)H, O—CH$_2$—Ph or O—(C$_1$–C$_4$)-alkyl;

(CH$_2$)$_m$-aryl or (CH$_2$)$_n$-heteroaryl, wherein m is 0–6 and aryl is phenyl, thienyl or pyridyl and the aryl moiety or the heteroaryl moiety may be optionally substituted up to two times by F, Cl, Br, OH, CF$_3$, O—(C$_1$–C$_6$)-alkyl, (CH$_2$)$_n$—SO$_2$—(C$_1$–C$_6$)-alkyl, (CH$_2$)$_n$—SO$_2$—NH$_2$, (CH$_2$)$_n$—SO$_2$—N(=CH—N(CH$_3$)$_2$), wherein n is 0–6, NH—SO$_2$—(C$_1$–C$_6$)-alkyl, NH—SO$_2$-phenyl, where the phenyl ring may be optionally substituted up to two times by F, Cl, CN, OH, (C$_1$–C$_6$)-alkyl, O—(C$_1$–C$_6$)-alkyl, CF$_3$, COOH, COO(C$_1$–C$_6$)-alkyl, CONH$_2$, where n is 0–6, COOH, COO(C$_1$–C$_6$)-alkyl, or CONH$_2$;

R5 is H;

R6 is Cl, Br, OH, O—(C$_1$–C$_6$)-alkyl, O—(CH$_2$)$_n$-aryl, or O—(CH$_2$)$_n$-heteroaryl, wherein n is 0–6 and aryl is phenyl and heteroaryl is 2-, 3- or 4-pyridyl or 2- or 3-thienyl;

O—C(O)—H, O—C(O)—(C$_1$–C$_6$)-alkyl, O—C(O)—(C$_3$–C$_8$)-cycloalkyl, O—C(O)-aryl, O—C(O)-heteroaryl, wherein aryl is phenyl and heteroaryl is pyridyl, thienyl or furanyl;

O-alpha- or -beta-glucuronic acid, SH, S—(C$_1$–C$_6$)-alkyl, S—(CH$_2$)$_n$-phenyl, wherein n is 0–6, S—C(O)—(C$_1$–C$_6$)-alkyl, S—C(O)—(C$_3$–C$_8$)-cycloalkyl, S—C(O)-phenyl; SO—(C$_1$–C$_6$)-alkyl, SO—(CH$_2$)$_n$-phenyl, wherein n is 0–6, SO$_2$—(C$_1$–C$_6$)-alkyl, SO$_2$—(CH$_2$)$_n$-phenyl, wherein n is 0–6, NH$_2$, NH—(C$_1$–C$_6$)-alkyl, NH—(C$_3$–C$_7$)-cycloalkyl, N[(C$_1$–C$_6$)-alkyl]$_2$, morpholin-4-yl, pyrrolidin-1-yl, piperidin-1-yl, piperazin-1-yl, 1-methylpiperazin-4-yl, 1-benzylpiperazin-4-yl, NH-phenyl, NH—CH$_2$-phenyl, NH—C(O)—(C$_1$–C$_6$)-alkyl or NH—C(O)-phenyl, or R5 and R6 together form =O, wherein n is 2–6, (C$_1$–C$_6$)-alkyl (C$_1$–C$_6$)-alkyl, CH$_2$-phenyl CH$_2$-phenyl, H$_3$C CH$_3$ or =NOH or =NOH and their physiologically acceptable salts and physiologically functional derivatives.

3. The compound of claim 1, wherein,

R1, R1' are independently selected from H, F, Cl, Br, —OH, O—(C$_1$–C$_6$)-alkyl or (C$_1$–C$_6$)-alkyl, wherein one of the hydrogens of the alkyl radicals may be replaced by OH;

R2 is H, (C$_1$–C$_6$)-alkyl or C(O)—(C$_1$–C$_6$)-alkyl;

R3 is Cl, Br, (CH$_2$)$_n$—COO(C$_1$–C$_6$)-alkyl, (CH$_2$)$_n$—COOH or (CH$_2$)$_n$—CONH$_2$, wherein n is 0 or 1;

R4 is (C$_1$–C$_4$)-alkyl or (C$_3$–C$_6$)-cycloalkyl, wherein one of the hydrogens of the alkyl radicals may be replaced by OH;

(CH$_2$)$_n$-aryl or (CH$_2$)$_n$-heteroaryl, wherein n is 0–6 and aryl is phenyl and heteroaryl is 1- or 2-naphthyl, 2-, 3- or 4-pyridyl or 2- or 3-thienyl and the aryl radical or heteroaryl radical may be optionally substituted up to two times by F, Cl, Br, OH, CF$_3$, O—(C$_1$–C$_6$)-alkyl, SO$_2$—(C$_1$–C$_6$)-alkyl, (CH$_2$)$_n$—SO$_2$—NH$_2$, where n is 0–6; (C$_1$–C$_6$)-alkyl, COOH, COO(C$_1$–C$_6$)-alkyl or CONH$_2$; or (CH$_2$)$_n$—A—R8, wherein n is 1–6;

A is O or SO$_2$;

R8 is (C$_1$–C$_8$)-alkyl, (C$_3$–C$_8$)-cycloalkyl, wherein one of the hydrogens of the alkyl radicals may be replaced by OH;

(CH$_2$)$_m$-aryl or (CH$_2$)$_m$-heteroaryl, where m is 0–6 and aryl is phenyl and heteroaryl is thienyl and the aryl moiety or the heteroaryl moiety may be optionally substituted up to two times by F, Cl, Br, OH, CF$_3$, O—(C$_1$–C$_6$)-alkyl, SO$_2$—(C$_1$–C$_6$)-alkyl, SO$_2$—NH$_2$, COOH, COO(C$_1$–C$_6$)-alkyl or CONH$_2$;

R5 is H;

R6 is OH or O—(C$_1$–C$_6$)-alkyl, wherein n is 0–6;

O—C(O)—(C$_1$–C$_6$)-alkyl, O—C(O)-aryl, O—C(O)-heteroaryl, wherein aryl is phenyl and heteroayl is thienyl;

O-alpha or -beta-glucuronic acid, SO$_2$—(C$_1$–C$_6$)-alkyl, SO$_2$—(CH$_2$)$_n$-phenyl, where n is 0–6, NH$_2$, morpholin-4-yl, NH—C(O)—(C$_1$–C$_6$)-alkyl or NH—C(O)-phenyl or R5 and R6 together form =O or

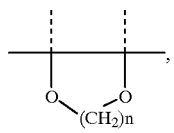

where n is 2–6,
and their physiologically acceptable salts.

4. A pharmaceutical composition, comprising one or more compounds as claimed in claim 1.

5. A pharmaceutical composition, comprising one or more compounds as claimed in claim 2.

6. A pharmaceutical composition, comprising one or more compounds as claimed in claim 3.

7. A pharmaceutical composition comprising one or more compounds as claimed in claim 1, and further comprising one or more anorectic active ingredients.

8. A pharmaceutical composition comprising one or more compounds as claimed in claim 2, and further comprising one or more anorectic active ingredients.

9. A pharmaceutical composition comprising one or more compounds as claimed in claim 3, and further comprising one or more anorectic active ingredients.

10. A method for the prophylaxis or treatment of obesity comprising administering to a patient in need thereof one or more compounds as claimed in claim 1.

11. The method of claim 10, further comprising administering an additional anorectic active agent.

12. A method for the prophylaxis or treatment of obesity comprising administering to a patient in need thereof one or more compounds as claimed in claim 2.

13. The method of claim 12, further comprising administering an additional anorectic active agent.

14. A method for the prophylaxis or treatment of obesity comprising administering to a patient in need thereof one or more compounds as claimed in claim 3.

15. The method of claim 14, further comprising administering an additional anorectic active agent.

16. A method for the prophylaxis or treatment of type II diabetes comprising administering to a patient in need thereof one or more compounds as claimed in claim 1.

17. The method of claim 16, further comprising administering an additional anorectic active agent.

18. A method for the prophylaxis or treatment of type II diabetes comprising administering to a patient in need thereof one or more compounds as claimed in claim 2.

19. The method of claim 18, further comprising administering an additional anorectic active agent.

20. A method for the prophylaxis or treatment of type II diabetes comprising administering to a patient in need thereof one or more compounds as claimed in claim 3.

21. The method of claim 20, further comprising administering an additional anorectic active agent.

22. A method for enhancing lipid metabolism comprising administering to a patient in need thereof one or more compounds as claimed in claim 1.

23. The method of claim 22, further comprising administering an additional anorectic active agent.

24. A method for enhancing lipid metabolism comprising administering to a patient in need thereof one or more compounds as claimed in claim 2.

25. The method of claim 24, further comprising administering an additional anorectic active agent.

26. A method for enhancing lipid metabolism comprising administering to a patient in need thereof one or more compounds as claimed in claim 3.

27. The method of claim 26, further comprising administering an additional anorectic active agent.

28. A process for preparing a pharmaceutical composition comprising one or more of the compounds as claimed in claim 1, which comprises mixing the active compound with a pharmaceutically suitable excipient and forming a composition suitable for administration.

29. A process for preparing a pharmaceutical composition comprising one or more of the compounds as claimed in claim 2, which comprises mixing the active compound with a pharmaceutically suitable excipient and forming a composition suitable for administration.

30. A process for preparing a pharmaceutical composition comprising one or more of the compounds as claimed in claim 3, which comprises mixing the active compound with a pharmaceutically suitable excipient and forming a composition suitable for administration.

31. A process for preparing compounds as claimed in claim 1, which comprises reacting, according to the equation below,

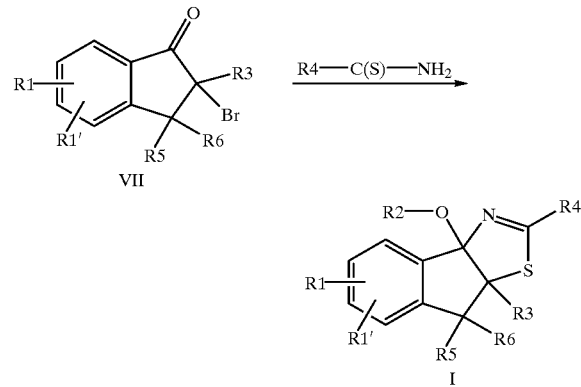

a compound of formula VII in which the radicals are as defined for formula I with a thioamide of formula R4—C(S)—NH$_2$, in which R4 is as defined for formula I to give compounds of formula I in which R2 is hydrogen.

32. The method of claim 31, further comprising derivatizing R2 to form compounds of formula I wherein R2 is a radical selected from the group consisting of ($C_1$–$C_6$)-alkyl, ($C_3$–$C_6$)-cycloalkyl, $(CH_2)_n$-phenyl, $(CH_2)_n$-thienyl, $(CH_2)_n$-pyridyl, $(CH_2)_n$-furyl, C(O)-($C_1$–$C_6$)-alkyl, C(O)-($C_3$–$C_6$-cycloalkyl, C(O)-$(CH_2)_n$-phenyl, C(O)-$(CH_2)_n$-thienyl, C(O)-$(CH_2)_n$-pyridyl and C(O)-$(CH_2)_n$-furyl, wherein n is 0–5 and in which any of phenyl, thienyl, pyridyl or furyl may be optionally substituted up to two times by Cl, F, CN, $CF_3$, ($C_1$–$C_3$)-alkyl, OH or O—($C_1$–$C_6$)-alkyl.

* * * * *